(12) United States Patent  
Nardini et al.

(10) Patent No.: US 8,784,428 B2  
(45) Date of Patent: Jul. 22, 2014

(54) DEVICE FOR MEASURING THE DEGREE OF BENDING OF AN INTRAMEDULLARY NAIL

(75) Inventors: Reto Nardini, Langendorf (CH); Adrian Baumgartner, Langendorf (CH); Urs Hulliger, Langendorf (CH)

(73) Assignee: Depuy Synthes Products, LLC, Raynham, MA (US)

( * ) Notice: Subject to any disclaimer, the term of this patent is extended or adjusted under 35 U.S.C. 154(b) by 200 days.

(21) Appl. No.: 13/236,126

(22) Filed: Sep. 19, 2011

(65) Prior Publication Data

US 2012/0239039 A1 Sep. 20, 2012

Related U.S. Application Data

(60) Provisional application No. 61/386,255, filed on Sep. 24, 2010.

(51) Int. Cl.  
*A61B 17/72* (2006.01)

(52) U.S. Cl.  
USPC .............................. 606/102; 606/64

(58) Field of Classification Search  
CPC ....................................... A61B 17/56  
USPC ........ 606/62–64, 67, 68, 102; 73/849; 33/793  
See application file for complete search history.

(56) References Cited

U.S. PATENT DOCUMENTS

| 3,239,938 A * | 3/1966 | Kaercher ..................... 33/793 |
| 4,982,613 A | 1/1991 | Becker |
| 5,065,631 A | 11/1991 | Ashpitel et al. |

FOREIGN PATENT DOCUMENTS

| DE | 10 2008 063 844 | 7/2010 |
| FR | 2 559 376 | 8/1985 |
| WO | 2007/025191 | 3/2007 |
| WO | 2008/017501 | 2/2008 |
| WO | 2008/105874 | 9/2008 |

* cited by examiner

*Primary Examiner* — Pedro Philogene  
*Assistant Examiner* — David Comstock  
(74) *Attorney, Agent, or Firm* — Fay Kaplun & Marcin, LLP

(57) ABSTRACT

A device for measuring a degree of bending of an intramedullary nail comprises a probe sized and shaped for insertion into a cannulation of an intramedullary nail. The probe including a first longitudinal element extending along a longitudinal axis from a distal end to a proximal end and a second longitudinal element extending along a longitudinal axis from a distal end to a proximal end, the distal ends of the first and second longitudinal elements attached to one another so that the longitudinal axes of the first and second longitudinal elements extend substantially parallel to each other and define a middle plane. A measuring element measures relative axial displacement of the proximal ends of the first and second longitudinal elements in the middle plane upon bending of the first and second longitudinal elements as the probe is inserted into a cannulation of the intramedullary nail.

19 Claims, 6 Drawing Sheets

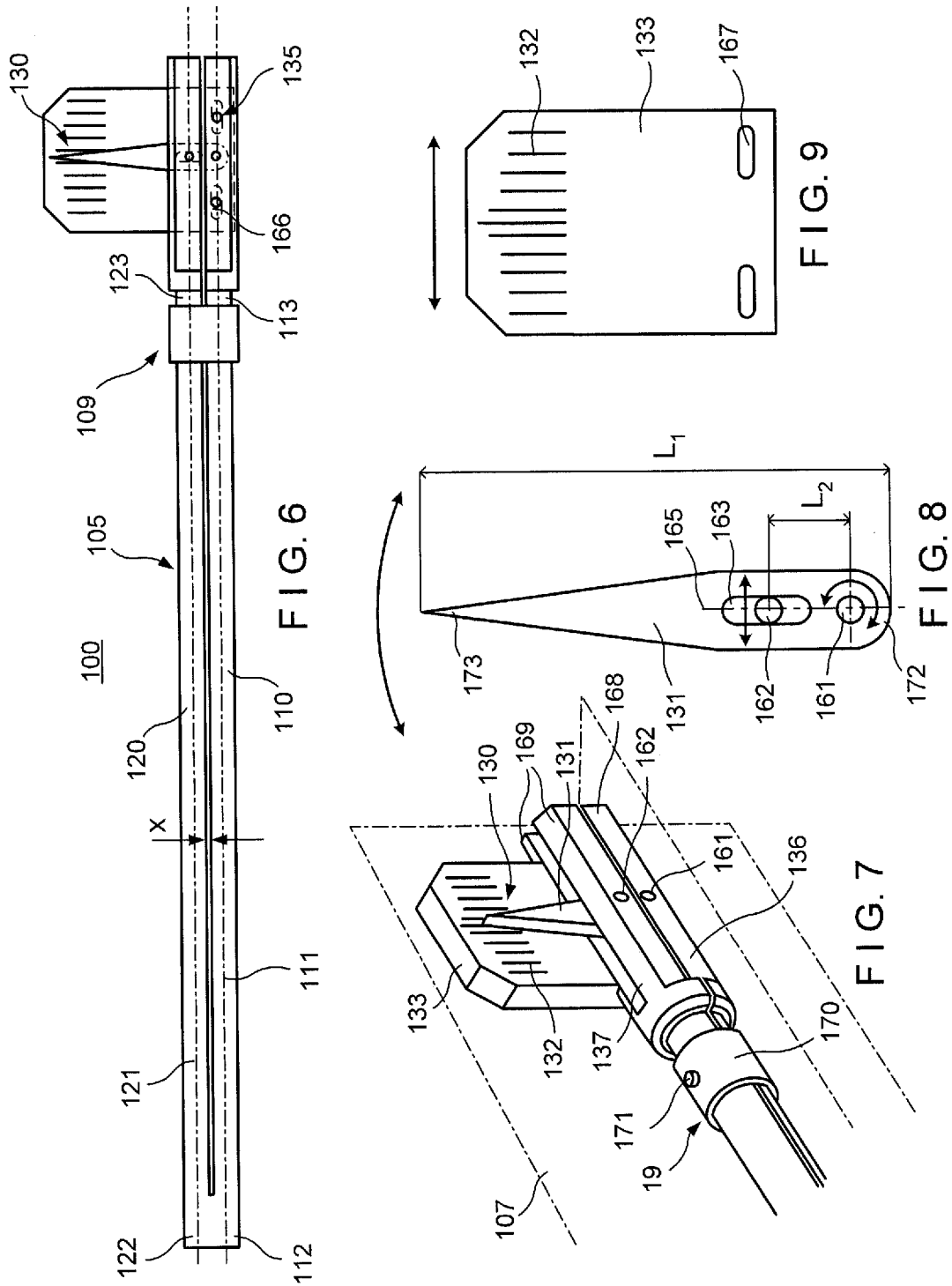

DEVICE FOR MEASURING THE DEGREE OF BENDING OF AN INTRAMEDULLARY NAIL

PRIORITY CLAIM

The present application claims priority to U.S. Provisional Application Ser. No. 61/386,255 entitled "Device for Measuring the Degree of Bending of an Intramedullary Nail" filed on Sep. 24, 2010 to Reto Nardini, Adrian Baumgartner and Urs Hulliger. The entire contents of this application are incorporated herein by reference thereto.

FIELD OF THE INVENTION

The present invention generally relates to a device for measuring bending strain. More particularly, the present invention relates to a device for measuring the degree of bending of an intramedullary nail. Exemplary embodiments of the present invention describe a device that may be inserted into a cannulation of an intramedullary nail to accurately determine a position of a transverse locking hole extending therethrough.

BACKGROUND

Intramedullary nails are often inserted into the medullary canals of bones to fix fractures. Such an intramedullary nail may be fixed relative to the bone via locking screws passed through transverse locking holes extending through the intramedullary nail. During insertion, however, intramedullary nails are often bent out of their normal curvature such that it is difficult to determine a position of the transverse locking holes. An aiming device may be used to guide a surgical instrument, such as a drill, and/or the locking screws through the transverse locking holes. However, purely mechanical aiming devices may not be reliable enough if, for example, the nail has bent in unpredictable way inside the bone. Current solutions employ x-ray imaging or electromagnetic tracking to determine the actual location of the transverse locking holes.

BRIEF SUMMARY OF THE INVENTION

The present invention relates to a measuring device that is based on a principle of measurement with an easily detectable physical quantity.

The present invention relates to a device for measuring the degree of bending of an intramedullary nail including a cannulation and a transverse locking hole. The device comprises a first longitudinal element extending along a longitudinal axis from a distal end to a proximal end and a second longitudinal element extending along a longitudinal axis from a distal end to a proximal end, the distal ends of the first and second longitudinal elements joined together so that the longitudinal axes of the first and second elements extend parallel to each other and define a middle plane in combination with a measuring mechanism measuring a relative axial displacement of the proximal ends of the first and second longitudinal elements in the middle plane upon bending of the first and second longitudinal element.

The device according to the present invention measures the relative displacement of the proximal ends of the first and second longitudinal elements in a middle plane of the device. Due to the principle of measurement used, some advantages of the device according to the present invention over prior art are that the device does not require electronics, has a simple design, low manufacturing price and is easy to use.

The device may be inserted into the cannulation of the intramedullary nail and will bend to correspond to a bend of the intramedullary nail such that proximal ends of the two longitudinal elements will move with respect to each other. This small but reliable relative movement of the proximal ends is used to quantify the deformation of the inserted nail.

The device measures the bending of the nail in a plane orthogonal to the axis of the locking hole. Any other possible deformations of the nail are negligible.

The measured value of the device may be transferable to other systems, e.g. a navigation system. This provides for a navigation solution which also covers the locking issue. The determined value can be used to calibrate a navigation system, where no mechanical aiming device is present. Alternatively, the measured value can be used to adjust a mechanical aiming device.

The device may be used for any application involving intramedullary nails (e.g., intramedullary nails for insertion in the femur, tibia and humerus.). Furthermore, the device may be constructed entirely of one or both of a synthetic material and a metal.

In an exemplary embodiment, the first and second longitudinal elements are spaced apart from each other orthogonal to their longitudinal axes by a distance x>0, preferably by a distance x which has a minimum value 0.1 mm, and more preferably by a distance x which has a minimum value of 0.25 mm.

In a further exemplary embodiment, the device has a cross sectional area orthogonal to the longitudinal axes with a height measured parallel to the distance between the longitudinal axes and a width orthogonal to the height and wherein the ratio of the width to the height is a minimum of 0.25, and preferably a minimum of 0.3.

In again a further exemplary embodiment, the device has a cross sectional area orthogonal to the longitudinal axes with a height measured parallel to the distance between the longitudinal axes and a width orthogonal to the height and wherein the ratio of the width to the height is a maximum of 0.8, and preferably a maximum of 0.7. This configuration has the advantage that the device can be bent in any plane along the central axis of the device. Thus, the device can adapt its shape to the shape of a spatially bent intramedullary nail when the device is inserted into the cannulation of the intramedullary nail.

In yet a further exemplary embodiment, the measuring element for measuring the bending of the intramedullary nail is mechanical and comprises an indicator, preferably a pointer actuated by a movement of one of the first and second longitudinal elements and a scale fixed or fixable to the other one of the first and second longitudinal elements.

In another exemplary embodiment, the pointer is rotatably arranged at a first base member extending from the proximal end of the first longitudinal element and actuated by a pin fixed to a second base member extending from the proximal end of the second longitudinal element and wherein the scale is arranged at the first base member. The pointer may have an overall length $L_1$ while an axis of rotation of the pointer is a length $L_2$ from an axis of the pin. Thus, due to the ratio of $L_1$ to $L_2$, an amplification of the measured value can be achieved, facilitating easy reading by a user of the device.

In another exemplary embodiment, the measuring element for measuring the degree of bending of the intramedullary nail is electronic. The displacement between the proximal ends of the first and second longitudinal element can be measured by, for example, a magnet and a Hall sensor, measuring a changing capacity using a capacitor measuring the distance between two metallic plates, measuring the tension wherein a piezoelectric crystal is compressed, measuring the inductance (e.g., via coils, mutual distance, etc), or optical measuring such as, for example, on CNC-machines, where precision markings are counted as they move.

In again another exemplary embodiment, the measuring element is hydraulic. In this embodiment, the displacement may be measured by compressing a tube containing liquid so that the liquid is forced to extend along a scale.

In still another exemplary embodiment, the measuring element comprises a zero setting mechanism. One of the advantages of this embodiment is that the measuring element is capable of being set to a zero position upon insertion of the device into the cannulation of an undeformed intramedullary nail (i.e., prior to insertion in the medullary cavity of a bone).

In yet another exemplary embodiment, the first and second longitudinal elements are spaced apart from each other orthogonal to their longitudinal axes by a distance x>0 and wherein the ratio of the distance x to the height of the device measured parallel to the distance x is a maximum of 0.5, and preferably a maximum of 0.25 mm. The difference of the bending radii of the first and second longitudinal element increases with an increasing distance x between the first and second longitudinal element. Thus, with an increasing distance x the relative axial displacement of the proximal ends of the first and second longitudinal element increases upon bending of the device.

In a further exemplary embodiment, the device comprises one or more spacers arranged between the first and second longitudinal element. Thus, first and second longitudinal element spaced apart by a distance x are not pressed against each other when the device is bent.

In a further exemplary embodiment, the device comprises a positioning element which rotationally fixes the device with respect to an intramedullary nail and which preferably provides for a defined insertion length of the device into the cannulation of the intramedullary nail.

In a further exemplary embodiment, the first and second longitudinal elements contact each other along a length thereof, between their proximal ends and their distal ends. Thus, the first and second longitudinal elements may slide relative to one another upon bending of the device so that the complete deformation of the device is consequently transferred into a relative displacement.

In a further exemplary embodiment, the length of the device may range from between approximately 20 cm-65 cm. For example, the device may have a length of about 45 cm.

In another exemplary embodiment, the bending of the device is in the range of 0° to ±3°, preferably in the range of 0° to ±1°. At the tip of the measuring device, and respectively of the intramedullary nail, this bending range may result in a deviation in the range of 0 to 20 mm, typically 10 mm. Preferably, the resulting relative axial displacement—as measured at the proximal ends—is in a range between about 0.5 mm 5 mm.

A further embodiment of the present invention, a kit may comprise a device, as described above, and an intramedullary nail with a cannulation and a transverse locking hole.

In accordance with another embodiment of the present invention, a method for setting a locking screw into an intramedullary nail is provided which comprises the step of mounting a mechanical aiming device onto one end of an intramedullary nail having a cannulation and a transverse locking hole, preferably onto the proximal end of the intramedullary nail; the aiming device having a bore hole which is aligned with the cannulation. A device according to the intention is then inserted through the borehole in the distal locking guiding device and into the cannulation of the intramedullary nail prior to insertion of the intramedullary nail into the intramedullary cavity. A guide bore in the distal locking guiding device is adjusted to the transverse locking hole via an adjustment mechanism arranged at the distal locking guiding device. The measuring element is set to a zero position and the device is removed from the intramedullary nail. The aiming device is removed from the intramedullary nail and the intramedullary nail inserted into the intramedullary cavity of a long bone. The mechanical aiming device is mounted onto the intramedullary nail and the device is inserted into the cannulation of the intramedullary nail. The relative axial displacement of the proximal ends of the first and second longitudinal elements is measured with the measuring element. The mechanical aiming device is then adjusted in relation to the measured relative axial displacement via the adjustment mechanism of the aiming device. A locking screw is set through the guide bore in the guide sleeve into the transverse locking hole.

In another exemplary embodiment, the guide bore may be adjusted in the distal locking guiding device by inserting a bolt into the guide bore and adjusting the extension arm of the distal locking guiding device until the bolt is coaxial to the transverse locking hole in the intramedullary nail.

BRIEF DESCRIPTION OF THE DRAWINGS

Several embodiments of the invention will be described in the following by way of example and with reference to the accompanying drawings in which:

FIG. 6 illustrates a lateral view of another exemplary embodiment of the device according to the present invention;

FIG. 7 illustrates magnified perspective view of the measuring element for measuring the relative axial displacement of the proximal ends of the first and second longitudinal elements of the embodiment of the device according to FIG. 6;

FIG. 8 illustrates a plane view of a pointer of the embodiment of the device according to FIG. 6;

FIG. 9 illustrates a plane view of the plate with a scale of the embodiment of the device according to FIG. 6;

DETAILED DESCRIPTION

Figure 1:
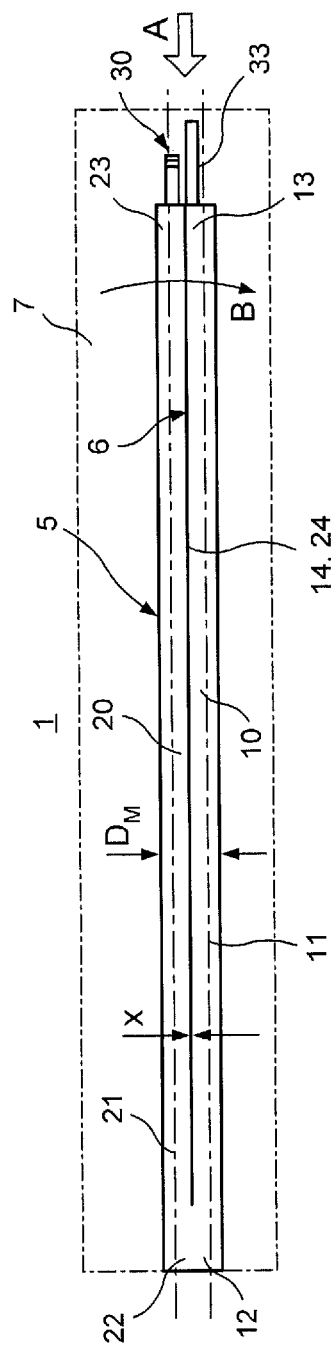
FIG. 1 illustrates a lateral view of an exemplary embodiment of the device according to the present invention.

The present invention may be further understood with reference to the following description and the appended drawings wherein like elements are referred to with the same reference numerals. The present invention relates to the treatment of fractures and, in particular, relates to devices for measuring a degree of curvature of an intramedullary nail that has been inserted into a medullary canal of a bone. Exemplary embodiments of the present invention describe a device comprising two longitudinal elements which move relative to one another upon insertion into the intramedullary nail to measure the degree of bending of the intramedullary nail.

As shown in FIGS. 1-4 and 10-12, a device 1 according to an exemplary embodiment of the present invention comprises a probe 5 that is sized and shaped for insertion into a cannulation 41 of an intramedullary nail 40 to measure a degree of bending of the intramedullary nail 40 via a measuring element 30. The degree of bending measured by the measuring element 30 may be used to adjust an aiming device 50 such that an aiming bore 55 thereof is properly aligned with a transverse locking hole 42 of the intramedullary nail 40. The probe 5, as shown in FIG. 1, includes a first longitudinal element 10 extending along a first longitudinal axis 11 from a distal end 12 to a proximal end 13 and a second longitudinal element 20 extending along a second longitudinal axis 21 from a distal end 22 to a proximal end 23. The distal ends 12, 22 of the first and second longitudinal elements 10, 20 may be fixed to one another such that the first and second longitudinal axes 11, 21 are parallel to one another and define a middle plane 7 of the probe 5. A central plane 8 of the probe 5 extends orthogonally to the middle plane 7, extending between the first and second longitudinal elements 10, 20 substantially equidistant from the longitudinal axes 11, 21 of the first and second longitudinal element 10, 20. In another exemplary embodiment, the distal end 12 of the first longitudinal element 10 may be integrally formed with the distal end 22 of the second longitudinal element 20 so that the probe 5 is formed as a single piece. The first and second longitudinal elements 10, 20 each have inner surfaces 14, 24, respectively, which face each other and are substantially planar. The first and second longitudinal elements 10, 20 may be fixed relative to one another so that only a thin slot 6 extends between the inner surfaces 14, 24 of the first and second longitudinal elements 10, 20.

Figure 4:
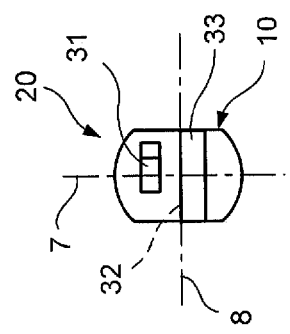
FIG. 4 illustrates a front view in the direction of arrow A, as shown in FIG. 1.
Figure 10:
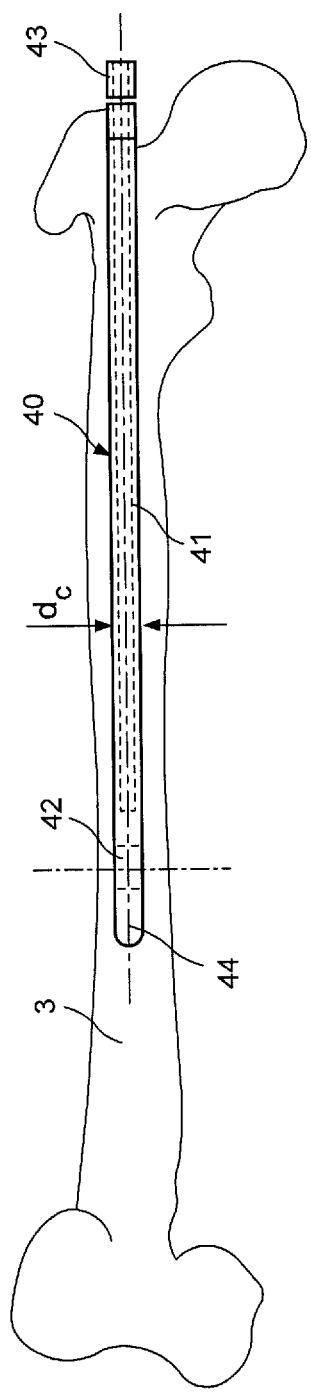
FIG. 10 illustrates side view of a femur with an intramedullary nail inserted in the medullary cavity.

As shown in FIG. 4, the first and second longitudinal elements 10, 20 may each have a laterally flattened semi-circular cross-section, each including a curved radially outermost surface and substantially planar lateral side surfaces. Due to the laterally flattened semi-circular cross-section of the first and second longitudinal elements 10, 20, a flexural rigidity of the probe 5 permits bending of the probe 5 in both the middle plane 7 and in the central plane 8. Thus, the probe 5 can adapt its shape to the shape of the spatially bent intramedullary nail 40 upon its insertion into the cannulation 41 of the intramedullary nail 40. The probe 5 has a diameter $D_M$ measured in the middle plane 7 from the radially outermost curved surface of the first longitudinal element 10 to the curved radially outermost surface of the second longitudinal element 20, which corresponds to an inner diameter $d_C$ of the cannulation 41 of an intramedullary nail 40 so that the probe 5 may be slidably inserted into the cannulation 41 of the intramedullary nail 40, as shown in FIG. 10. In an alternative embodiment, each of the first and second longitudinal elements 10, 20 may be circular, oval or polygonal in cross-section (e.g. rectangular). It will be understood by those of skill in the art that the cross-sections of the first and second longitudinal elements 10, 20 may take any of a variety of shapes so long as the probe 5 is sized and shaped for insertion into the cannulation 41 so that bends in the intramedullary nail 40 are transferred to the probe 5.

When, for example, the probe 5 is bent in direction B, as shown in FIG. 1, the first longitudinal axis 11 of the first longitudinal element 10 has a bending radius smaller than that of the second longitudinal axis 21 of the second longitudinal element 20. The differing bending radii of the first and second longitudinal axes 11, 21 causes the proximal ends 13, 23 of the first and second longitudinal elements 10, 20, respectively, to be displaced relative to one another. The probe 5 is configured to measure the degree of bending of the probe 5 in the middle plane 7 which coincides with the drawing plane in FIG. 1.

Figure 2:
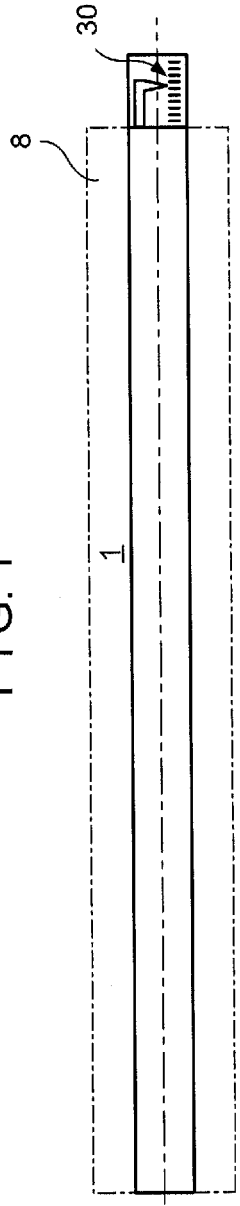
FIG. 2 illustrates a top view of the embodiment of the device according to FIG. 1.
Figure 3:
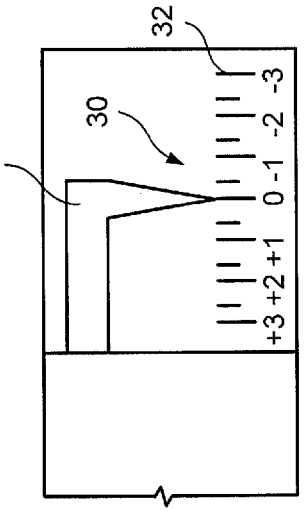
FIG. 3 illustrates magnified view of the measuring element for measuring the relative axial displacement of the proximal ends of the first and second longitudinal elements of the embodiment of the device according to FIG. 1.

The measuring element 30, as shown in FIG. 2, is attached to the proximal ends 13, 23 of the first and second longitudinal elements 10, 20 and is configured to measure the relative displacement of the proximal ends 13, 23 of the first and second longitudinal elements 10, 20 when the probe 5 is bent. As shown in FIG. 3, the measuring element 30 is completely mechanical, and includes a scale 32 and a pointer 31.

The pointer 31 is fixed to a proximal face at the proximal end 23 of the second longitudinal element 20 and may be substantially hook shaped including a fixed leg extending proximally from the proximal end 23 parallel to the second longitudinal axis 21 of the second longitudinal element 20 and a pointed leg extending orthogonally to the middle plane 7, substantially perpendicular to a proximal end of the fixed leg.

The scale 32 may be arranged on a surface of a plate 33 axially protruding from the proximal end 13 of the first longitudinal element 10. The surface of the plate 33 including the scale 32 may be coplanar or parallel to the inner surface 14 of the first longitudinal element 10. Thereby, the scale 32 extends proximally from the proximal end 13 along the middle plane 7 or parallel thereto. The scale 32 may be divided into first and second parts.

The first part may include markings ranging from 0 to +3 provided in increasing order in a direction towards the distal end 12 of the first longitudinal element 10. The second part may include markings ranging from 0 to −3 provided in the opposite direction. When the probe 5 is bent in the drawing plane with a center of curvature located on the same side of the central plane 8 as the first longitudinal element 10 as indicated by arrow B in FIG. 1, the bending radius of the first longitudinal element 10 is smaller than the bending radius of the second longitudinal element 20 so that the pointer 31 is displaced relative to the scale 32 in the first part with the markings from 0 to +3. When the probe 5 is bent in an opposite direction in the drawing plane with a center of curvature located on the same side of the central plane 8 as the second longitudinal element 20 the bending radius of the first longitudinal element 10 is larger than the bending radius of the second longitudinal element 20 so that the pointer 31 is displaced relative to the scale 32 in the second part with the markings from 0 to −3. Although the markings are specifically described as ranging from −3 to +3, it will be understood by those of skill in the art that the markings may take any of a variety of forms, e.g., numerical markings varying in range, symbolic markings, etc.

Figure 11:
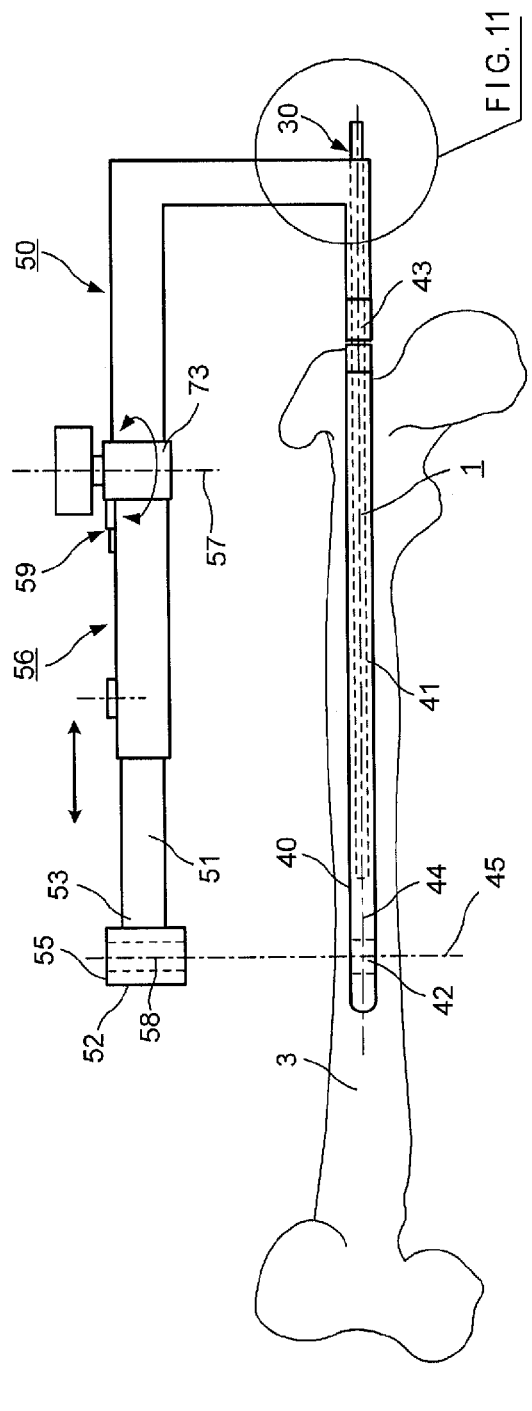
FIG. 11 illustrates a side view of a femur with an intramedullary nail, a guiding device attached to the intramedullary nail and the embodiment of the device according to FIGS. 1 and 2.
Figure 12:
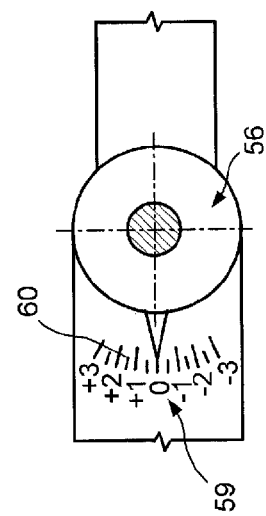
FIG. 12 illustrates a top view onto the articulation of the extension arm of the guiding device according to FIG. 11.

The measurements obtained by the measuring element 30 may be used to adjust an aiming device 50 such that an aiming bore 55 thereof aligns with a transverse locking hole 42 of the intramedullary nail 40. The aiming device 50 may be adjusted via an adjusting mechanism 56. The scale 32 of the measuring element 30, however, may not necessarily be metrically scaled. Thus, to facilitate the transfer of the measured value from the device 1 to the adjustment mechanism 56 of the distal locking guiding device 50, as shown in FIG. 11, the adjustment mechanism 56 may include an indicating element 59 with a scale 60 having a scale division that corresponds to the markings of the scale 32, as shown in FIG. 12. Calibration of the measuring element 30 and the corresponding indicating element 59 of the adjustment mechanism 56 of the aiming device 50 and the scale 32 of the measuring element 30 allows for a simple adjustment of the aiming device 50 without the need to convert a measured value to a particular angle to be set on the adjustment mechanism 56 of the distal locking guiding device 50.

Figure 5:
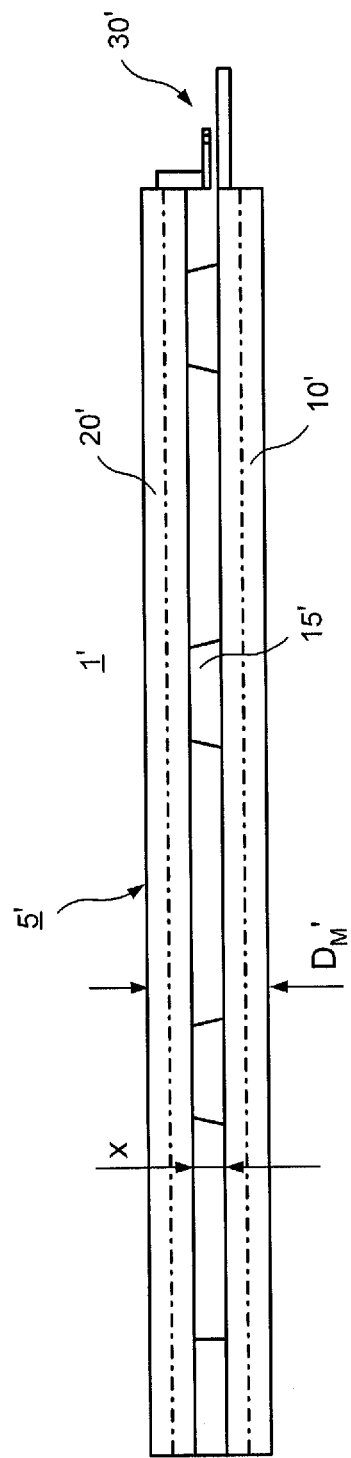
FIG. 5 illustrates a lateral view of a further exemplary embodiment of the device according to the present invention.

As shown in FIG. 5, a device 1' according to a further embodiment of the present invention is substantially similar to the device 1, as described above, but comprises a probe 5' including first and second longitudinal elements 10', 20', respectively, spaced from one another by a distance x. The distance x between the first and second longitudinal elements 10', 20' increases a difference between the bending radii of the first and second longitudinal elements 10', 20'. Similarly to the device 1, first and second longitudinal axes 11', 21' of the first and second longitudinal element 10', 20' are substantially parallel such that the first and second longitudinal elements 10', 20' are spaced apart from each other orthogonal to the first and second longitudinal axes 11', 21'. The distance x may be about 30% of a diameter $D_{M}{'}$ of the probe 5'. Due to a larger difference of the bending radii of the first and second longitudinal axes 11', 21' upon bending of the probe 5' to a certain angle, a larger relative axial displacement of proximal ends 13', 23' of the first and second longitudinal element 10', 20' can be achieved. Further, a pointer 31 may be stepped so that the pointing tip is closer to a surface of a plate 33' with a scale 32'. To prevent the first and second longitudinal elements 10', 20' from being pressed against one another due to bending of the probe 5' in the middle plane 7, a plurality of spacers 15' are arranged between the inner surfaces 14, 24 of the first and second longitudinal element 10', 20'. Thereby, the plurality of spacers 15 can be affixed to or formed integrally with one or alternatingly with one of each of the first and second longitudinal elements 10', 20'.

FIGS. 6 to 9 illustrate another embodiment of a device 100 for measuring a degree of bending of an intramedullary nail 40 which has been inserted into a medullary canal of a bone. The device 100 is substantially similar to the device 1 described above and comprises a probe 105 including first and second longitudinal elements 110, 120 attached to one another at distal ends 112, 122, respectively, thereof and a measuring element. The device 100 may be used in a manner similar to that described for the device 1, as shown in FIGS. 10-13, so that the measured degree of bending may be used to adjust the aiming device 50. The device 100, however, differs from the device 1 in that the measuring element 30 is configured differently than on the device 1 and additionally comprises a positioning element 109 permitting the device 100 to be rotationally fixed relative to the intramedullary nail 40 in which the probe 105 is inserted and which defines an insertion length of the probe 105 into the cannulation 41 of the intramedullary nail 40.

Similarly to the device 1, the first and second longitudinal elements 110, 120 may have any or a variety of cross-sectional shapes. For example, the cross-section of each of the first and second longitudinal elements 110, 120 may be semicircular. Alternatively, the first and second longitudinal element 110, 120 may have a radially outermost surface, a first part of which extends along a curve that is substantially circular and which includes substantially planar lateral surfaces. In another embodiment, each of the first and second longitudinal elements 110, 120 may have a circular, oval or polygonal, e.g. rectangular, cross-sectional shape.

The measuring element 130 also similarly comprises a pointer 31 and a scale 32 arranged on a plate 33. The measuring element 130, however, further comprises a zero setting mechanism 135 to adjust the zero position of the scale 32 relative to the pointer 31 in a direction along a first and second longitudinal axis 111, 121 of the first and second longitudinal elements 110, 120, respectively. The pointer 131 and the plate 133 including the scale 132 are mounted on first and second base members 136, 137 fixed to or integrally formed with a proximal end 113 of the first longitudinal element 110 and a proximal end 123 of the second longitudinal element 120, respectively, so that the first and second base members 136, 137 are displaced relative to each other by a distance substantially similar to a displacement between the proximal ends 113, 123 of the first and second longitudinal elements 110, 120 when the probe 105 is bent. Each of the first and second base members 136, 137 may have a generally U-shaped configuration, including a pair of lateral legs 168, 169, respectively, extending parallel to a middle plane 107 from a closed end at the proximal end 113, 123 of the first and the second longitudinal elements 110, 120.

The pointer 131 extends from a first end 172 that may be pivotally coupled to the first base member 136 to a second pointed end 173. The pointer 131 may be coupled to the first base member 136 between the lateral legs 168 of the first base member 136 via a first pin 161 passing through a bore hole 164 at a first end of the pointer 131 and a corresponding hole through the first base member 136 so that the first pin 161 is affixed to the first base member 136. Thus, the second end 171 of the pointer 131 extends laterally past the second base member 137. The pointer 131 may thus pivot about the axis of the first pin 161 wherein the axis of the first pin 161 extends orthogonally to the middle plane 107 of the device 100. The pointer 131 may also include an elongated opening 163 extending therethrough and elongated along a central axis 165 extending along a length of the pointer 131. A second pin 162 is affixed to the second base member 137, with the axis of the second pin 62 being parallel to the axis of the first pin 61, and passed through the elongated opening 163. Upon relative axial displacement of the proximal ends 113, 123 of the first and second longitudinal elements 110, 120, the first and second base members 136, 137 and, consequently, the first and second pins 161, 162 are identically displaced relative to each other. Thus, the pointer 31 is pivoted about the first pin 61 and the tip of the pointer 31 moves relative to the scale 32. The pointer 131 may have a length $L_1$ while the first and second pins 161, 162 are positioned a length $L_2$ from one another. Thus, due to a ratio of the length $L_1$ of the pointer 131 to the length $L_2$ between the axes of the first and second pin 161, 162 the pointed tip at the second end 173 of the pointer 131 moves at a larger extent than the axial displacement of the proximal ends 113, 123 of the first and second longitudinal elements 110, 120 so that an amplification of the measured value results.

The scale 132 may be arranged on a surface of a plate 133 protruding from the second base member 137 transverse to the longitudinal axes 111, 121 of the first and second longitudinal elements 110, 120. A surface of the plate 133 including the scale 132 is parallel to the middle plane 107. The scale 132 may include markings substantially similar to the markings described above in regard to the scale 132 of the embodiment of the device 1, as shown in FIGS. 1 to 4. The plate 133 may be affixed to the first base member 136 such that the plate 133 extends laterally therefrom via two screws 166 including threads which engage corresponding internal threads in the first base member 136. The plate 133 may include two elongated holes 167 through which the screws 166 pass through to fix the plate 133 to the first base member 136. The holes 167 may have a major axis extending parallel to the longitudinal axes 111, 121 of the first and second longitudinal elements 110, 120 such that the plate 133 may be moved longitudinally relative to the probe 105. Thus, to adjust the zero position of the scale 132 relative to the pointer 131 the screws 66 may be loosened to allow the plate 132 to be displaced relative to the pointer 131 in a direction along the first and second longitudinal axes 111, 121 of the first and second longitudinal elements 110, 120 until the second end 173 of the pointer 132 points to the zero position of the scale 132. Once the zero position has been achieved as desired, the screws 166 may be fastened to fix the plate 133 relative to the probe 105 and the pointer 131.

Figure 13:
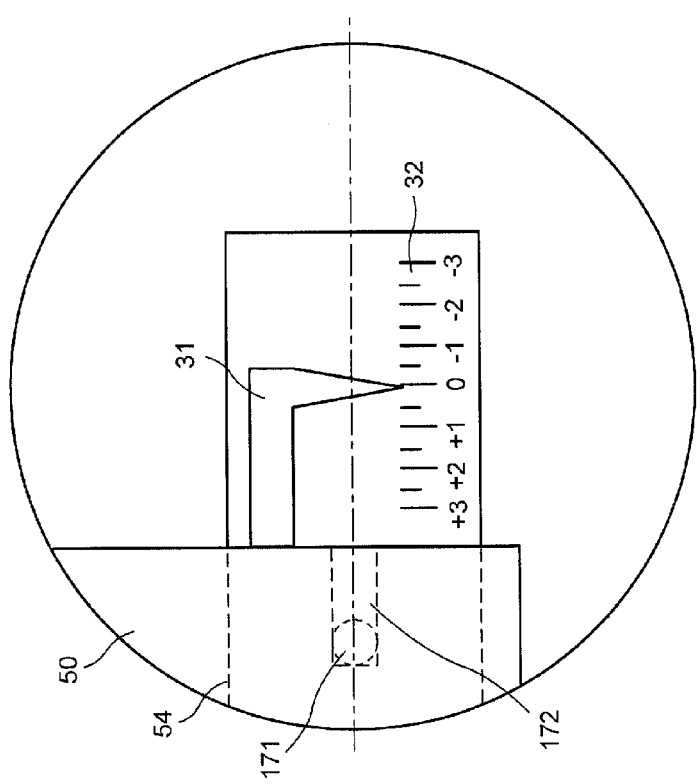
FIG. 13 illustrates a magnified view of the detail C in FIG. 11.

The positioning mechanism 109 of the device 100 comprises a sleeve 170 surrounding the proximal ends 111, 121 of the first and second longitudinal elements 110, 120. The sleeve 170 may be slid over the first and second longitudinal elements 110, 120 and fixed to one of the first and second longitudinal elements 110, 120 via a pin 171. The pin 171 may protrude from an exterior surface of the sleeve 170 so that the pin 171 engages a corresponding groove 172, as shown in FIG. 13, along an inner surface of the borehole 54 of the aiming device 50, as shown in FIG. 12. When the aiming device 50 is attached to the intramedullary nail 40 in a desired rotational position and the device 100 is inserted into the cannulation 41 of the intramedullary nail 40 through the bore hole 54 the pin 171 engaging the groove 172 provides a defined rotational placement of the device 100 with respect to the intramedullary nail 40, as shown in FIG. 13, and provides a defined insertion length of the probe 105 into the cannulation 41 of the intramedullary nail 40. As also shown in FIG. 13, it will be understood by those of skill in the art that the positioning element 109, as described in reference to the device 100, may also be included in any of the devices 1, 1', as described above.

Although the intramedullary nail 40 and the aiming device 50 shown in FIGS. 10-13 have been specifically described in reference to the device 1, it will be understood by those of sill in the art that the intramedullary nail 40 and the aiming device 50 may be similarly used with the device 1' and the device 100. The devices 1, 1', 100 may be used to measure a degree of bending of an intramedullary nail 40 which has been inserted into the medullary cavity of a femur 3, as shown in FIG. 10. The intramedullary nail 40 extends along a longitudinal axis 44 from a proximal end 43 to a distal end 44 and includes a cannulation 41 extending from the proximal end 43 along a portion of a length thereof with a diameter $d_C$ and a distal transverse locking hole 42 extending therethrough.

FIGS. 11 to 13 illustrate the intramedullary nail 40 inserted into the medullary cavity of the femur 3 with an aiming device 50 attached thereto and the device 1 inserted in the cannulation 41 of the intramedullary nail 40. The aiming device 50 is fixed to the proximal end 43 of the intramedullary nail 40 in a rotatively defined position such that a borehole 54 at a proximal end thereof is aligned with the cannulation 41 of the intramedullary nail 40. The guiding device 50 may further comprise an extension arm 51 which extends generally parallel to the longitudinal axis 44 of the intramedullary nail 40 and which comprises a guide sleeve 52 at a distal end 53 thereof. The guide sleeve 52 has a guide bore 55 which extends through the sleeve 52 transversely relative to the longitudinal axis 44. The guide sleeve 52 may be aligned with the locking hole 42 of the intramedullary nail to guide a drill bit coaxially of an axis of the transverse locking hole 42 to drill a hole in the distal portion of the femur 3 into which a distal locking screw may be inserted. The extension arm 51 may be adjusted such that the sleeve 52 is both rotationally adjustable relative to a remaining portion of the arm 51 and longitudinally movable relative to the remaining portion of the arm 51. Specifically, the extension arm 51 may include an adjustment mechanism 56 having a releasably lockable articulation 73 with an axis of rotation 57 and an indicating element 59 indicating an angulation of the extension arm 51 so that the sleeve 52, and thereby the guide bore 55, is rotatable relative to the remaining portion of the arm 51. The indicating element 59 may include a scale 60 having scale markings that correspond to the scale markings of the scale 32 of the measuring element 30, as shown in FIG. 12. Further, the extension arm 51 is telescopically configured so that the sleeve 52 is longitudinally movable relative to the remaining portion of the arm 51. When, after insertion of the intramedullary nail 40 into the medullary cavity of the femur 3, the probe 5 is inserted into the cannulation 41 of the intramedullary nail 40, the probe 5 axially adapts to the shape of the cannulation 41 of the intramedullary nail 40 so that the bending strain of the probe 5 corresponds to the bending strain of the intramedullary nail 40. The probe 5 of the device 1 is inserted into the cannulation 41 of the intramedullary nail through the borehole 54 in the guiding device 50. The scale 60 of the indicating means 59 of the adjustment mechanism 56 of the distal locking guiding device 50 corresponds in scale division (e.g., markings) to the scale 32 of the device 1. The device 100 may be similarly inserted into the intramedullary nail 40, but may also be rotatively fixed relative to the nail 40 and the aiming device 50 via the positioning mechanism 109. In particular, the pin 171 extending laterally from the outer surface of the sleeve 170 is pressed into the groove 172 along an inner surface of the borehole 54.

A method for setting a locking screw into an intramedullary nail 40 may comprise the step of calibrating the aiming device 50 and/or the measuring element 30 including mounting a mechanical aiming device 50 onto one end of an intramedullary nail 40, which has not yet been inserted into a bone. The intramedullary nail 40 may have a cannulation 41 and a transverse locking hole 42. Although the aiming device 50 is shown as a distal aiming device attached to the proximal end 43 of the nail 40 for guiding instruments to the locking hole 42 proximate a distal end 44, it will be understood by those of skill in the art that the aiming device 50 may be used for guiding instruments to any locking hole along the intramedullary nail 40. The aiming device 50 is attached to the intramedullary nail 40 so that a proximal borehole 54 of the aiming device 50 is aligned with the cannulation 41. The probe 5 of the device 1 may then be inserted through the borehole 54 in the aiming device 50 into the cannulation 41 of the intramedullary nail 40. The guide sleeve 52, and thereby the guide bore 55, of the aiming device 52 may be adjusted to align the transverse locking hole 42. The adjustment mechanism 56 arranged on the aiming device 50 is adjusted such that the scale markings thereon correspond to the scale markings shown on the scale 32 of the measuring element 30. The adjustment may include an adjustment of the length of the telescopable extension arm 51 and/or an adjustment of the angulation of the extension arm 51 about the axis of rotation 57 of the articulation 73. This step may be performed by inserting a bolt into the guide bore 55 and adjusting the extension arm 51 of the distal locking guiding device 50 until the bolt is coaxial to the axis 45 of the transverse locking hole 42 in the intramedullary nail 40.

Once the extension arm 51 of the aiming device 50 has been adjusted such that the guide bore 55 is aligned with the transverse locking hole 42, the measuring element 30 of the device 1 and the indicating element 59 of the adjustment mechanism 56 are set into the zero position. The device 1 may then be removed from the intramedullary nail 40. The guiding device 50 may also be removed from the intramedullary nail 40. The intramedullary nail 40 may then be inserted into the intramedullary cavity of a long bone such as for example, the femur 3. Once inserted, the aiming device 50 is mounted onto one of the proximal and distal ends 43, 44 of the intramedullary nail 40 in the same rotational position described above in regard to the calibration procedure. The device 1 is inserted into the cannulation 41 of the intramedullary nail 40.

Insertion of the device 1 into the cannulation 41 measures the degree of bending of the intramedullary nail 40 caused by the insertion of the nail 40 into the bone by measuring the relative axial displacement of the proximal ends 13, 23 of the first and second longitudinal elements 10, 20 via the measuring element 30. The aiming device 50 may be adjusted using the displacement measured by the measuring element 30. The adjustment mechanism 56 of the aiming device 50 may then be adjusted to correspond to the measurement indicated on the scale 32 of the measuring element 30. This adjustment step comprises an adjustment of the angulation of the extension arm 51 via adjustment of the articulation 73. The adjustment of the length of the telescopable extension arm 51 is only used during the calibration procedure. When the probe 5 is bent in a plane orthogonal to the drawing plane with a center of curvature located on the same side of the central plane 8 as the first longitudinal element 10, indicated by arrow B in FIG. 1, the bending radius of the first longitudinal element 10 is smaller than the bending radius of the second longitudinal element 20 so that the pointer 31 is displaced relative to the scale 32 in the first part with the markings from 0 to +3. When the probe 5 is contrarily bent in the plane orthogonal to the drawing plane with a center of curvature located on the same side of the central plane 8 as the second longitudinal element 20 the bending radius of the first longitudinal element 10 is larger than the bending radius of the second longitudinal element 20 so that the pointer 31 is displaced relative to the scale 32 in the second part with the markings from 0 to −3. The measured value may be simply transferred from the scale 32 of the device 1 to the adjustment mechanism 56 of the distal locking guiding device 50 since the scale 32 of the device 1 has substantially identical scale divisions as the scale 60 of the indicating means 59 of the adjustment mechanism 56 of the aiming device 50. Once the extension arm 51 has been properly adjusted so that the guide bore 55 aligns with the locking hole 42, tools, such as a drill, or other instruments may be inserted therethrough. Once a corresponding hole has been drilled in the femur 3, the locking screw may be inserted through the guide bore 55 of the guide sleeve 52, into the corresponding hole in the femur 3 and into the transverse locking hole 42 of the intramedullary nail 40 to fix the intramedullary nail 40 relative to the femur 3.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A device for measuring a degree of bending of an intramedullary nail, comprising:
a probe sized and shaped for insertion into a cannulation of an intramedullary nail, the probe including a first longitudinal element extending along a longitudinal axis from a distal end to a proximal end and a second longitudinal element extending along a longitudinal axis from a distal end to a proximal end, the distal ends of the first and second longitudinal elements attached to one another so that the longitudinal axes of the first and second longitudinal elements extend substantially parallel to each other and define a middle plane; and
a mechanical measuring element configured to mechanically measure relative axial displacement of the proximal ends of the first and second longitudinal elements in the middle plane upon bending of the first and second longitudinal elements as the probe is inserted into a cannulation of the intramedullary nail.

2. The device according to claim 1, wherein an outer profile of the probe is selected to substantially match an inner profile of a cannulation of an intramedullary nail within which it is to be deployed so that, as the probe traverses the cannulation, the probe is bent in a manner corresponding to the bending of the nail.

3. The device according to claim 2, wherein the first and second longitudinal elements are spaced apart from each other by one of a distance x=0.1 mm and x=0.25 mm.

4. The device according to claim 1, wherein the device has a cross sectional area orthogonal to the longitudinal axes with a height measured parallel to the distance between the longitudinal axes and a width orthogonal to the height and wherein the ratio of the width to the height is at least one of 0.25 and 0.3 and at most one of 0.7 and 0.8.

5. The device according to claim 1, wherein the measuring element includes a pointer coupled to one of the first and second longitudinal elements and a scale which, in an operative configuration, is fixed to the other of the first and second longitudinal elements.

6. The device according to claim 5, wherein the pointer is rotatably arranged at a first base member extending from the proximal end of the first longitudinal element and actuated by a pin fixed to a second base member extending from the proximal end of the second longitudinal element and wherein the scale is arranged at the first base member.

7. The device according to claim 1, wherein the measuring element includes a zero setting mechanism.

8. The device according to claim 1, wherein the first and second longitudinal elements are spaced apart from each other orthogonal to their longitudinal axes by a distance x >0, wherein the ratio of the distance x to the height of the device measured parallel to the distance x is at most one of 0.25 and 0.5.

9. The device according to claim 1, wherein the device further comprises at least one spacer arranged between the first and second longitudinal elements.

10. The device according to claim 1, further comprising a positioning element to define a rotational placement of the device with respect to the intramedullary nail and provide a defined insertion length of the device into the cannulation of the intramedullary nail.

11. The device according to claim 1, wherein the first and second longitudinal elements contact each other along a length thereof, between each of the proximal ends and the distal ends.

12. The device according to claim 1, wherein the length of the device ranges from between approximately 20 cm to approximately 65 cm.

13. The device according to claim 1, wherein the bending of the device is in the range of 0° to ±3°.

14. The device according to claim 13, wherein the bending of the device is in the range of 020 to ±120.

15. A system, comprising:
a device for measuring a degree of bending of the intramedullary nail, comprising:
a probe sized and shaped for insertion into a cannulation of an intramedullary nail, the probe including a first longitudinal element extending along a longitudinal axis from a distal end to a proximal end and a second longitudinal element extending along a longitudinal axis from a distal end to a proximal end, the distal ends of the first and second longitudinal elements attached to one another so that the longitudinal axes of the first and second longitudinal elements extend substantially parallel to each other and define a middle plane; and
a mechanical measuring element configured to mechanically measure relative axial displacement of the proximal ends of the first and second longitudinal elements in the middle plane upon bending of the first and second longitudinal elements as the probe is inserted into a cannulation of the intramedullary nail; and
an aiming device including an extension arm that is adjustable to correspond to a measured relative axial displacement of the proximal ends of the first and second longitudinal elements, the aiming device including a guide bore which, when the aiming device is adjusted, aligns with the locking hole of the intramedullary nail.

16. A method for setting a locking screw into an intramedullary nail comprising the steps of:
inserting a probe of a device into a cannulation of an intramedullary nail, the probe including a first longitudinal element extending along a longitudinal axis from a distal end to a proximal end and a second longitudinal element extending along a longitudinal axis from a distal end to a proximal end, the distal ends of the first and second longitudinal elements attached to one another so that the longitudinal axes of the first and second longitudinal elements extend substantially parallel to each other and define a middle plane; and
measuring a relative axial displacement of the proximal ends of the first and second longitudinal elements using a mechanical measuring element upon bending of the first and second longitudinal elements as the probe is inserted into a cannulation of the intramedullary nail.

17. The method according to claim 16, further comprising:
calibrating the device by inserting the device into the cannulation of the intramedullary nail prior to insertion of the intramedullary nail into bone and setting the measuring element to a zero position to correspond to a bending of the intramedullary nail in an undeformed configuration.

18. The method according to claim 16, further comprising:
adjusting an aiming device to correspond to the relative axial displacement measured by the measuring element.

19. The method according to claim 17, wherein calibrating the device further includes adjusting an aiming device such that a guide bore thereof aligns with a transverse locking hole of the undeformed intramedullary nail.

* * * * *

UNITED STATES PATENT AND TRADEMARK OFFICE
CERTIFICATE OF CORRECTION

PATENT NO. : 8,784,428 B2  
APPLICATION NO. : 13/236126  
DATED : July 22, 2014  
INVENTOR(S) : Nardini et al.

It is certified that error appears in the above-identified patent and that said Letters Patent is hereby corrected as shown below:

IN THE CLAIMS:

COLUMN 13 LINES 13-14

Claim 14 should be amended as follows:

-- 14. The device according to claim 13, wherein the bending of the device is in the range of 0° to ± 1°. --

Signed and Sealed this  
Twenty-seventh Day of January, 2015

Michelle K. Lee  
*Deputy Director of the United States Patent and Trademark Office*